(12) United States Patent
Werner et al.

(10) Patent No.: US 11,976,082 B2
(45) Date of Patent: *May 7, 2024

(54) CONTINUOUS PROCESS FOR MANUFACTURING ALKYL 7-AMINO-5-METHYL-[1,2,5]OXADIAZOLO[3,4-B]PYRIDINE-CARBOXYLATE

(71) Applicant: Boehringer Ingelheim International GmbH, Ingelheim am Rhein (DE)

(72) Inventors: Bernd Werner, Pfungstadt (DE); Tobias Alt, Ingelheim am Rhein (DE); Andrew T. Brusoe, New Milford, CT (US); Frederic Gerard Buono, Franklin Park, NJ (US); Michael Klumb, Mainz (DE); Bjoern Stahl, Ginsheim (DE); Thomas G. Tampone, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 194 days.

This patent is subject to a terminal disclaimer.

(21) Appl. No.: 17/326,383

(22) Filed: May 21, 2021

(65) Prior Publication Data
US 2021/0363157 A1 Nov. 25, 2021

(30) Foreign Application Priority Data

May 22, 2020 (EP) .................... 20176117

(51) Int. Cl.
C07D 498/04 (2006.01)
B01J 19/00 (2006.01)

(52) U.S. Cl.
CPC .......... *C07D 498/04* (2013.01); *B01J 19/002* (2013.01); *B01J 2219/00029* (2013.01);
(Continued)

(58) Field of Classification Search
CPC .................. C07D 498/04; B01J 19/002; B01J 2219/00029; B01J 2219/00033
See application file for complete search history.

(56) References Cited

U.S. PATENT DOCUMENTS 9,802,954 B2 * 10/2017 Pouzet ................ C07D 495/04
2008/0275057 A1 11/2008 Kawabe
(Continued)

FOREIGN PATENT DOCUMENTS

JP 2004516327 A 6/2004
JP 2008538759 A 11/2008
(Continued)

OTHER PUBLICATIONS

Joe V. D'Souza, "Pyrazine Condensations from Malononitrile", J. Indian Chem. Soc., 1984, 61, 10, p. 885-887 (Year: 1984).*
(Continued)

*Primary Examiner* — Valerie Rodriguez-Garcia
*Assistant Examiner* — Josmalen M. Ramos-Lewis
(74) *Attorney, Agent, or Firm* — David L. Kershner

(57) ABSTRACT

This invention relates to a novel continuous process for making alkyl 7-amino-5-methyl-[1,2,5]-oxadiazolo¬[3,4-b]pyridine-carboxylate,

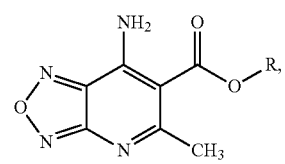

wherein R is $C_{1-3}$-alkyl. The process of the invention present invention overcomes disadvantages of processes of the prior
(Continued)

Continuous Flow Portion of Process

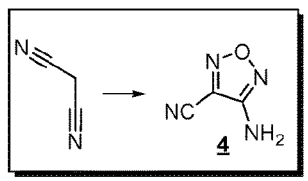 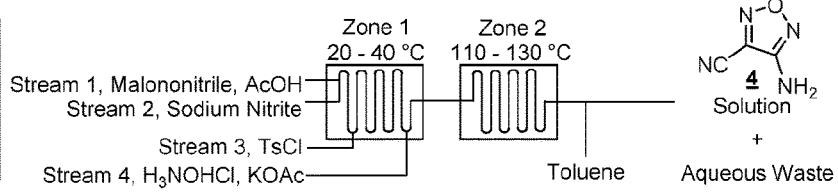 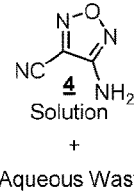

Batch Portion of Process art by avoiding the highly energetic intermediates, using readily available and inexpensive starting materials and reagents, and avoiding the isolation of intermediates. The process according to the invention is suitable for use on industrial scale.

19 Claims, 2 Drawing Sheets

(52) U.S. Cl.
CPC .............. *B01J 2219/00033* (2013.01); *B01J 2219/00051* (2013.01); *B01J 2219/00162* (2013.01)

(56) References Cited

U.S. PATENT DOCUMENTS

| | | | |
|---|---|---|---|
| 2012/0009560 | A1 | 1/2012 | Coupe et al. |
| 2015/0018547 | A1 | 1/2015 | Takakura et al. |
| 2021/0038603 | A1 | 2/2021 | Trieselmann et al. |
| 2021/0040077 | A1 | 2/2021 | Trieselmann et al. |

FOREIGN PATENT DOCUMENTS

| | | | | |
|---|---|---|---|---|
| JP | 2010526083 | A | 7/2010 | |
| WO | 02051845 | A2 | 7/2002 | |
| WO | 2006114405 | A2 | 11/2006 | |
| WO | 2008152403 | | 6/2008 | |
| WO | 2008101017 | | 8/2008 | |
| WO | 2008134690 | A1 | 11/2008 | |
| WO | 2008141843 | A1 | 11/2008 | |
| WO | WO-2008141843 | A1 * | 11/2008 | ........... C07D 215/44 |
| WO | 2010007255 | | 1/2010 | |
| WO | 2010007251 | | 6/2010 | |
| WO | 2010007253 | | 6/2010 | |
| WO | 2010070252 | | 6/2010 | |
| WO | 2011006497 | | 1/2011 | |
| WO | 2011114148 | A1 | 9/2011 | |
| WO | 2011160630 | | 12/2011 | |
| WO | 2011160633 | | 12/2011 | |
| WO | 2013092703 | | 6/2013 | |
| WO | 2004082383 | | 8/2013 | |
| WO | 2013125732 | A1 | 8/2013 | |
| WO | 2013192388 | | 12/2013 | |
| WO | 2014041195 | | 3/2014 | |
| WO | 2015073281 | A1 | 5/2015 | |
| WO | 2016044467 | | 3/2016 | |
| WO | 2016123275 | | 8/2016 | |
| WO | 2016168222 | | 10/2016 | |
| WO | 2016168225 | | 10/2016 | |
| WO | 2017070680 | A1 | 4/2017 | |
| WO | 2018024653 | | 2/2018 | |
| WO | 201844663 | A1 | 3/2018 | |
| WO | 2019149657 | A1 | 8/2019 | |
| WO | 2019149658 | A1 | 8/2019 | |
| WO | 2019149659 | A1 | 8/2019 | |
| WO | 2019149660 | A1 | 8/2019 | |

OTHER PUBLICATIONS

Giovanni Sartori, et al. "Protection (and Deprotection) of Functional Groups in Organic Synthesis by Heterogeneous Catalysis." Chem. Rev. 2004, 104, 199-250 (Year: 2004).*
Izabela Węglarz, et al. "Zinc Acetate Catalyzed Enantioselective Reductive Aldol Reaction of Ketones," I. Węglarz, M. Szewczyk, J. Mlynarski, Adv. Synth. Catal. 2020, 362, 1532 (Year: 2020).*
Joule, J. A., Mills, K, Smith, G. F. (2010). Heterocyclic Chemistry (1st ed.). CRC Press. (Year: 2010).*
Brainly.in. (Feb. 11, 2017). Difference between hydroxylamine hydrochloride and hydroxylammonium chloride. https://brainly.in/question/1695177 (Year: 2017).*
Ichikawa, Central Research Labs, A new Synthesis of Adenine and 4-Aminoimdazole-5-carboxamide, 1965.
International Search Report for PCT/EP2021/063090 mailed Jul. 1, 2021.
International Search Report for PCT/EP2021/063088 mailed Jul. 1, 2021.
International Search Authority and Written opinion, for PCT/EP2017/069274, dated Sep. 15, 2017.
Kuppens, "Elelvated Ration of acylated to unacylated ghrelin in children and young adults with Prader-Willi syndrome", Endocrine, Humana Press, vol. 50, No. 3, 2015, p. 633-642.
Vasil. Russian Chem Bulletin, Reactions of cyanoturazans with [beta]-dicarbonyl compiunds, 2001, vol. 50, p. 1280-1286.
Hirozane, SLAS Discovery, Identification and Characterization of a new series of Ghrelin O-Acyl Transferase Inhibitors, vol. 23, 2018.
Vasil, Mendellev Communications, Effective Synthesis of Funtionalized furazano, 1994, vol. 2, p. 57-58.
Hirozane, Identification and Characterization of a new series of Ghrelin O-Acyl Transferase Inhibitors, SLAS Discoery, 2017.
Haffner, Intensive Lifestyle Intervention or Metformin on Inflammation and Coagulation in Participants with Impaired Glucose Tolerance, The Diabetes Prevention Research Group, vol. 54, 2007.
Cummings, A preprandial rise in plasma ghrelin, Diabetes, vol. 50, 2001.
Druce, Ghrelinincreases foodintake in obese as well as lean subjects, Int J. of Obesity, vol. 29, 2005.
Zhang, Effect of Des0acyl Ghrelinon Adiposity and Glucose Metabolism, Endocrinology, 2008.
Wierup, The ghrelin cell, Regulatory peptides, vol. 107, 2002.
Broglio, Non-Acelated Ghrelin Counteracts the metabolic but not the neuroendocrine response, J. of Endocrine & Metabolism, vol. 80, 2004.
Delparigi, High circulating Ghrelin, J. Of Endocrinology & Metabolism, vol. 12, 2002.
Granata, Acylated and Unacylated Ghrelin promote Proliferation and inhibit Apositis of pancreatic B-cells and Human Islets, Endocrinology, vol. 2, 2007.
Granata, Des-Acyl Ghrelin Fragment and analogues promote survival of pancreatic b-cells, ACS, vol. 55, 2012.
Andrianov, Synthesis and Properties of 4-aminoo-3-cyanofurazan, Chem of heterocyclic Compunds, vol. 30, 1994.
Pagoria, Synthesisand Characterization of mutlicyclic oxadiazoles, Chem. of Heterocyclic Compunds, vol. 53, 2017, p. 760-778.
Bohle, Nucelophilic Addition of Hydroxylamine, J. Org Chem, 2000.
Vasil'ev, Effective Synthesis of Functionalized Furazano, Zelinsky Institute of Organix Chem., 1993.
Vasil'ev, Reaction of Cyanofurans, Russian Chem. Bulletin, vol. 50, 2001, p. 1280-1286.
Jordan, Tamoxifen: A most unlikely pioneering medicine: Nature, vol. 2, 2003, 9 pages.
Hackam, Translation of Research evidence from animals to Humans, JAMA, vol. 14, 2006, 5 pages.
Vasilyv, Reactions of Cyanofurazans with B-dicarbonyl compunds, Russian Chem Bulletin, vol. 50, 2001, 10 pages.
Vydshak, Application of Nickel Complexes, Russain J. of General Chem., vol. 90, 2020, p. 1439-1446.

* cited by examiner

Continuous Flow Portion of Process

Batch Portion of Process

35% overall yield

CONTINUOUS PROCESS FOR MANUFACTURING ALKYL 7-AMINO-5-METHYL-[1,2,5]OXADIAZOLO [3,4-B]PYRIDINE-CARBOXYLATE

FIELD OF THE INVENTION

This invention relates to a novel technical scale process for making alkyl 7-amino-5-methyl-[1,2,5]-oxadiazolo[3,4-b]pyridine-carboxylate 5 using continuous flow reaction conditions. Alkyl 7-amino-5-methyl-[1,2,5]oxadiazolo[3,4-b]pyridine-carboxylate 5 is a key intermediate for preparing compounds described in WO 2018/024653, WO 2019/149657, WO 2019/149658 and WO 2019/149659.

BACKGROUND OF THE INVENTION

The synthesis of the 4-amino-1,2,5-oxadiazole-3-carbonitrile 4 via the intermediates 6 and 7 was described by T. Ichikawa et al. (J. Heterocycl. Chem. 1965, 253).

Scheme 1

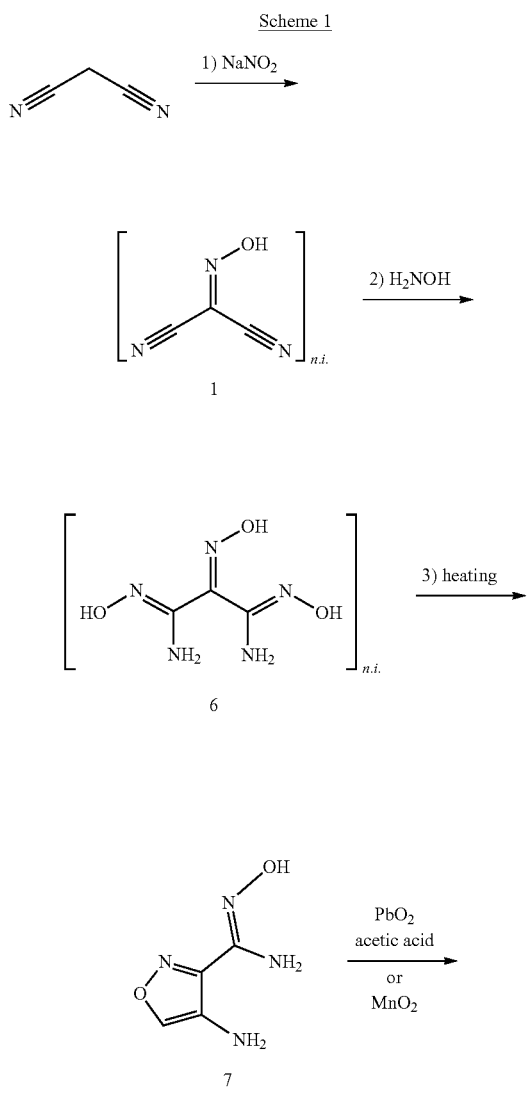

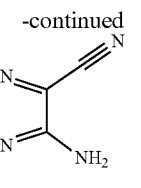

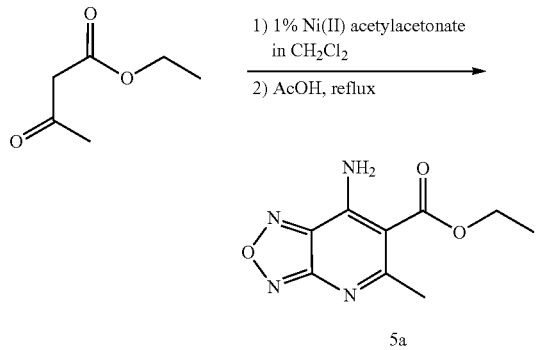

n.i. = not isolated

In 2017, P. F. Pagoria et al. published a modification of Ichikawa's route with improved yield and purity (Chem. Heterocycl. Compounds 2017, 53, 760).

The main drawback of the literature synthesis of 4-amino-1,2,5-oxadiazole-3-carbonitrile 4 is that the intermediate compounds 6 and 7 (as well as compound 4 are highly energetic substances. D. S. Bohle et al. describe that compound 6 "explodes at about 130° C. during DSC experiments, shattering the sample cup" (J. Org. Chem 2000, 65, 1139). Moreover, to induce the cyclization of compound 6 to the oxadiazole 7, the aqueous reaction mixture has to be heated under reflux. This may cause safety issues, particularly in the upscale of this transformation.

Another important drawback of the literature synthesis is the use of lead compounds for the deoximation of oxadiazole 7 to the oxadiazole 4. The use of toxic lead during the preparation of pharmaceuticals is questionable, anyway. However, in the majority of the literature descriptions, the lead is even used in stoichiometric amounts or higher. Thus, the weight load of lead compound in relation to substrate is high. As a result, a lot of toxic lead waste is generated.

As an alternative to the lead containing reagents, WO 2018/44663 describes the use of manganese(IV) oxide as a mild oxidation agent. However, due to the formation of the amide as a side product in significant amounts, the crude product was purified by column chromatography. This is a severe drawback for technical scale, as in large scale, column chromatography is very time-consuming and costly. Moreover, the risk of the highly energetic intermediates will not be overcome by this approach.

A. B. Sheremetev and V. A. Dorokhov et al. showed that ethyl acetoacetate adds to the nitrile group of 4-amino-1,2,5-oxadiazole-3-carbonitrile 4 in the presence of catalytic amounts of nickel(II) acetylacetonate in methylene chloride. By adding acetic acid and heating, ethyl 7-amino-5-methyl-[1,2,5]oxadiazolo[3,4-b]pyridine-carboxylate 5a is obtained via intramolecular cyclisation (Mendeleev Communication 1994, 4, 57; Russian Chemical Bulletin, Int. Ed., 2001, 50, 1280).

DETAILED DESCRIPTION OF THE INVENTION

Figure 1:
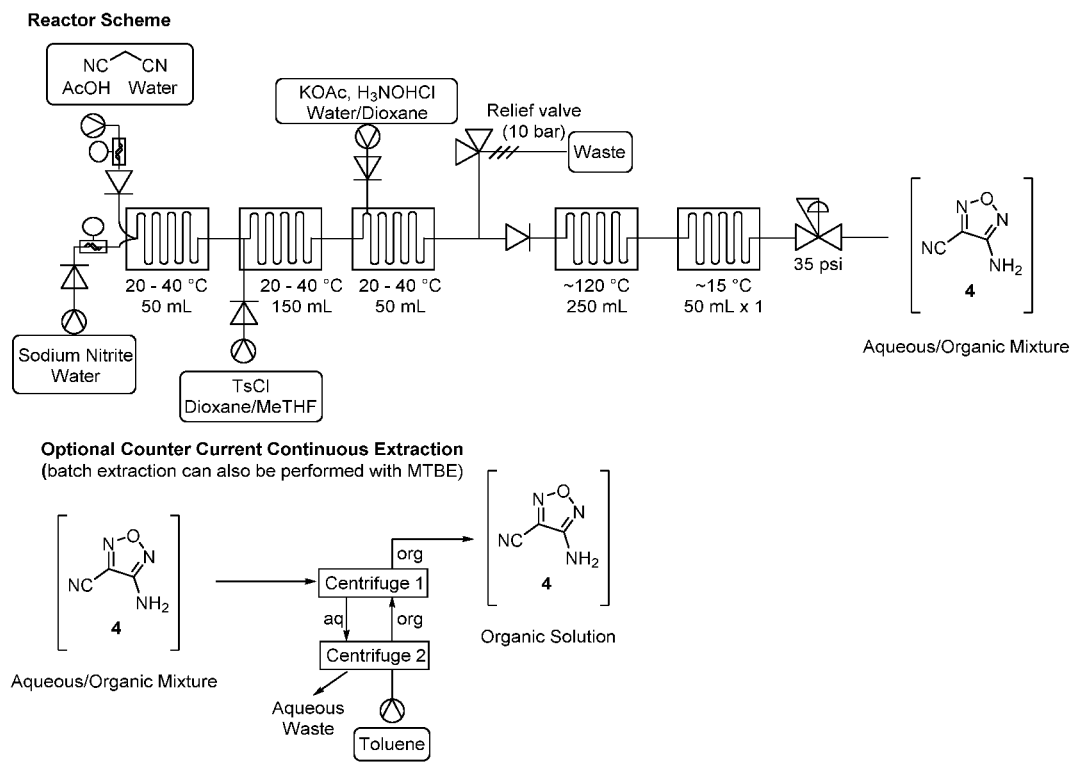
FIG. 1 shows the overall reactor scheme of the claimed process.

The present invention provides a process for manufacturing alkyl 7-amino-5-methyl-[1,2,5]-oxadiazolo[3,4-b]pyridine-carboxylate 5

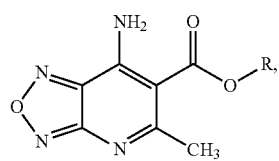

5 wherein R is $C_{1-3}$-alkyl,
by combining an integrated continuous flow system under overpressure, with a batch reactor, said process comprising the following steps:
(a) reacting malononitrile with sodium nitrite in the presence of a suitable acid, preferably in the presence of acetic acid, in a suitable solvent;
(b) reacting the reaction mixture obtained by step (a) with a suitable toluenesulfonic acid derivative, preferably with p-toluenesulfonyl chloride, to obtain compound 2;

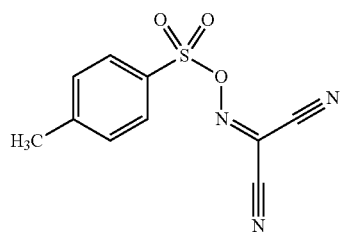

2

(c) reacting compound 2, in a suitable solvent with hydroxylamine or a suitable hydroxylamine salt to obtain compound 3;

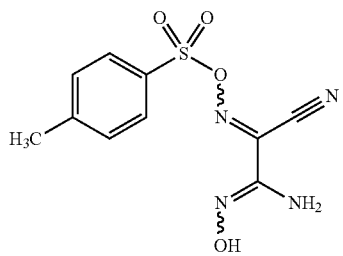

3

(d) cyclisation of compound 3 in the presence of a base under heating to about 120° C., in a suitable solvent to obtain the oxadiazole 4;

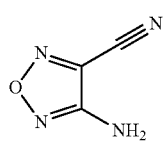

4

(e) removal of the by-product water formed in step (d) from the reaction mixture by phase separation;
(f) in situ-condensation of compound 4 in the reaction mixture obtained after step (e) with the appropriate beta-keto ester of formula

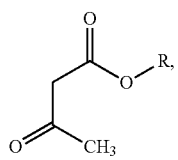

wherein R is $C_{1-3}$-alkyl,
in a batch reactor in the presence of a Lewis acid such as zinc acetate in a suitable solvent; and
(g) isolating compound 5 from a batch reactor.

In the above process, the beta-keto ester is a $C_{1-3}$-alkyl beta-keto ester. Preferably, the ethyl beta-keto ester is used. Correspondingly, in scheme 2 below, R is $C_{1-3}$-alkyl. Preferably, R is ethyl.

The process according to the invention is suitable for use on industrial scale.

Scheme 2

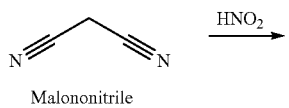

Malononitrile

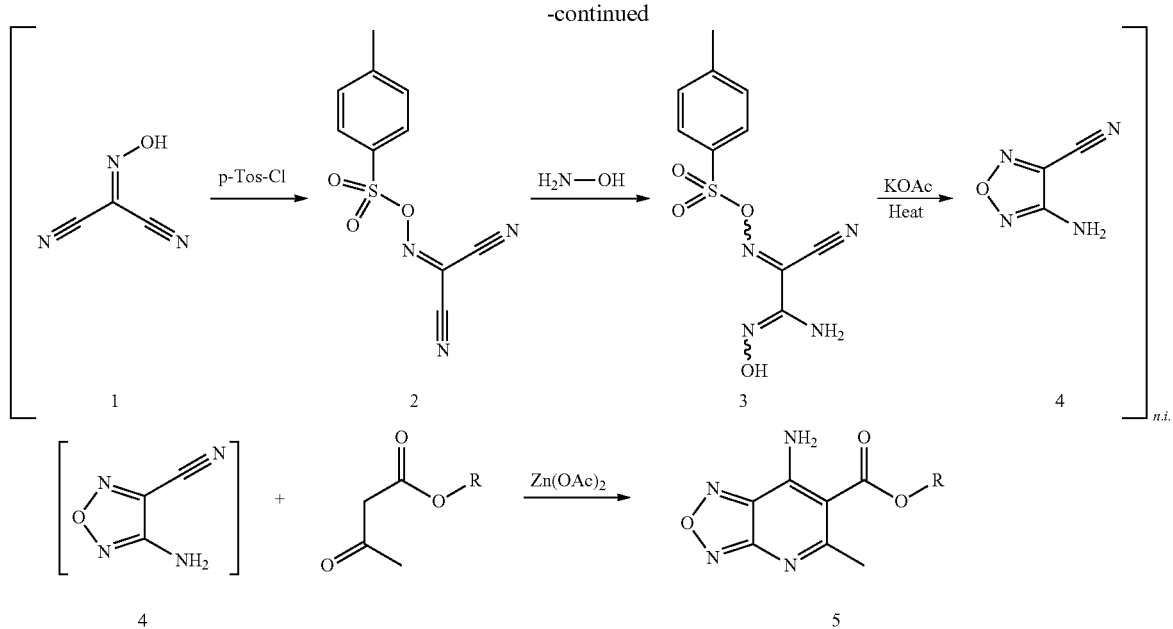

(n.i. = not isolated)
Synthesis of 1-4: Continuous Flow
Synthesis and Isolation of 5: Batch The flow process according to the present invention overcomes the disadvantages of processes of the prior art by having the distinction of
1) avoiding the highly energetic intermediates 6 and 7,
2) making use of inexpensive and readily accessible starting material and reagents,
3) avoiding the isolation of any intermediates, so that only the final product needs to be isolated,
4) eliminating the accumulation of all intermediates except 4,
5) avoiding the distillation of the solutions containing highly energetic intermediate 4,
6) yielding alkyl 7-amino-5-methyl-[1,2,5]-oxadiazolo[3,4-b]pyridine-carboxylate 5 in high purity with high average yield for each step,
7) reducing the overall solvent need for all five steps by approx. 60% as compared to the analogous batch processes.

Step (a)
Suitable acids for step (a) include hydrohalic acids like hydrochloric acid and hydrobromic acid, or organic acids like acetic acid. Preferably, acetic acid is used.
A suitable solvent for step (a) is water.
Step (a) is preferably carried out at a temperature of 20 to 40° C. for 15 s to 5 min, preferably at a temperature of about 30° C.
The whole continuous flow process is preferably carried out in a system with overpressure of at least 2 bar. The overpressure is caused by gas evolution due to the chemical reaction in step (a) and by superheating solvents in step (d) and is maintained by a backpressure regulator near the end of the reactor. Preferably, the overpressure is between 2 and 15 bar, more preferably between 6 and 10 bar.

Step (b)
Suitable toluenesulfonic acid derivatives useful as reagents for step (b) include p-toluenesulfonic acid anhydride and p-toluenesulfonic acid chloride. Preferably, p-toluenesulfonic acid chloride is used.

Suitable solvents for step (b) include ethereal solvents like 2-methyl-tetrahydrofuran (2-MeTHF) and 1,4-dioxane as well as water, and the mixtures thereof.
Step (b) is preferably carried out at a temperature of 20 to 40° C. for 15 s to 5 min, more preferably at a temperature of about 30° C.

Step (c)
Suitable solvents for step (c) include ethers like 2-methyl-tetrahydrofuran (2-MeTHF) and 1,4-dioxane and water, and mixtures thereof.
Step (c) is preferably carried out at a temperature of 20 to 40° C. for 15 s to 5 min, more preferably at a temperature of about 30° C.
Suitable hydroxylamine salts include hydroxyl ammonium chloride and hydroxyl ammonium sulfate. Hydroxyl ammonium chloride is preferred. Suitable bases for step (c) include organic bases like triethylamine or inorganic bases like alkali acetates, alkali carbonates and alkali hydrogencarbonates. Examples for suitable acetates are lithium acetate, sodium acetate, and potassium acetate. Examples for suitable carbonates are sodium carbonate and potassium carbonate. Examples for suitable hydrogencarbonates are sodium hydrogencarbonate and potassium hydrogencarbonate. Preferably, potassium acetate is used.

Step (d)
Suitable bases for step (d) include organic bases like triethylamine or inorganic bases like alkali acetates, alkali carbonates and alkali hydrogencarbonates. Examples for suitable acetates are lithium acetate, sodium acetate, and potassium acetate. Examples for suitable carbonates are sodium carbonate and potassium carbonate. Examples for suitable hydrogencarbonates are sodium hydrogencarbonate and potassium hydrogencarbonate. Preferably, potassium acetate is used.
Suitable solvents for step (d) include ethers like 1,4-dioxane and 2-methyl-tetrahydrofuran (2-MeTHF) as well as water, and the mixtures thereof.

Step (d) is preferably carried out at a temperature of 110 to 130° C., more preferably at a temperature of about 120° C. for 15 s to 5 min and under a pressure of at least 2 bar.

Step (e)

Step (e) may be conducted in a continuous or batch manner, preferably at about 20 to 45° C. by the use of a centrifugal extractor or batch reactor and with non-polar solvents as an extraction solvent. Heptane, isopropylacetate, methyl tert-butyl ether and toluene are suitable non-polar extraction solvents. The use of toluene or methyl tert-butyl ether as the solvent is preferred for continuous extraction. Most preferred for continuous extraction is the use of methyl tert-butyl ether as the solvent at a temperature of about 30° C. Methyl tert-butyl ether is preferred for batch extraction.

Step (f)

The appropriate beta-keto ester for step (f) is selected from the group consisting of a $C_{1-3}$-alkyl beta-keto ester. Preferably, the ethyl beta-keto ester is used.

Suitable Lewis acids for step (f) includes zinc salts like zinc acetate. Both zinc acetate dihydrate as well as anhydrous zinc acetate may be used. Preferably, zinc acetate dihydrate is used as Lewis acid.

Suitable solvents for step (f) include ethers like 1,4-dioxane, 2-methyl-tetrahydrofuran (2-MeTHF) and methyl tert-butyl ether, alcohols like ethanol, non-polar solvents like toluene, and any mixtures thereof. The preferred ether is 1,4-dioxane and the preferred alcohol is ethanol.

Step (f) is preferably carried out at a temperature of 60 to 100° C., more preferably at a temperature of about 70° C. for 2-24 h.

Step (g)

In step (g), compound 5 is preferably isolated by distillation to remove toluene and 2-methyl-tetrahydrofuran (2-MeTHF) and precipitated via addition of an antisolvent like water and isolated via filtration.

Alternatively, reacting the MTBE extract of 4 in ethanol to yield 5 allows either to crystallize and isolate 5 by simple addition of antisolvent water or by additional solvent distill off during the reaction time towards 5, increasing the space-time-yield of the overall yield.

Equipment

A suitable flow reactor for steps (a)-(d) contains design features to promote mixing (such as impingement points or static mixers), especially for steps (b) and (c), is resistant to corrosion (e.g. such as glass or Hastelloy), is capable of safely withstanding operating pressures of up to 15 bar, has a backpressure regulator to minimize or prevent boiling of solvents, is capable of rapidly heating and cooling (about 50 W per kg/h=180 kJ/g to keep selectivity), and has residence volumes long enough for the reactions to occur to completion. Additional safety features (such as relief valves, check valves) are optional. Pumps should be chosen based on their ability to pump at the necessary flow rates and pressures, preferably pulsation-free, at least with low pulsation.

FIG. 1 shows the overall reactor scheme of the claimed process.

General Definitions

Terms not specifically defined herein should be given the meanings that would be given to them by one of skill in the art in light of the disclosure and context.

In case a compound of the present invention is depicted in form of a chemical name and as a formula, in case of any discrepancy, the formula shall prevail.

Unless specifically indicated, throughout the specification and the appended claims, a given chemical formula or name shall encompass tautomers, rotamers and all stereo, optical and geometrical isomers (e.g. enantiomers, diastereomers, including E/Z isomers etc. . . . ) and racemates thereof as well as mixtures in different proportions of the separate enantiomers, mixtures of diastereomers, or mixtures of any of the foregoing forms where such isomers and enantiomers exist, as well solvates thereof such as for instance hydrates.

Abbreviations s seconds min minutes

A % area percentage

EXPERIMENTAL SECTION

Note: all intermediates are highly energetic compounds and toxic gases are generated as byproducts. Special care has to be taken on safety measures.

Example 1

Synthesis of ethyl 7-amino-5-methyl-[1,2,5]-oxadiazolo[3,4-b]pyridine-carboxylate 5 with Continuous Extraction (Steps a-g of the Overall Synthesis)

Figure 2:
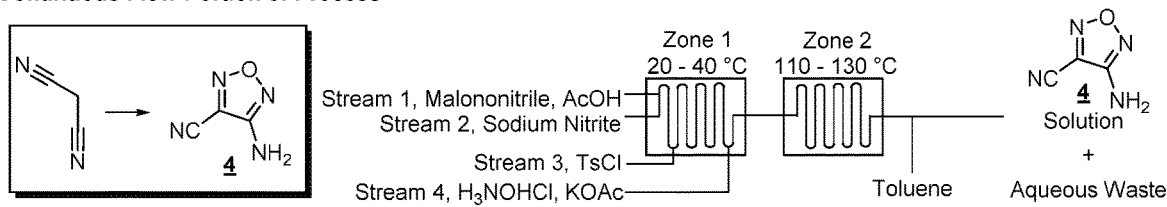
FIG. 2 shows the synthesis of ethyl 7-amino-5-methyl-[1,2,5]-oxadiazolo-[3,4-b]pyridine-carboxylate 5 with continuous extraction. (Steps a-g correspond to the overall synthesis.)
Figure 2:
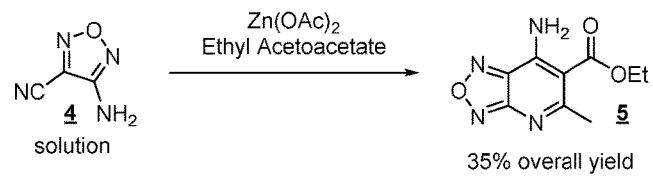

The synthesis of compound 5 is depicted in FIG. 2.

1. A solution of malononitrile (1.00 kg) in water (7.22 kg) and acetic acid (0.955 kg) was prepared in a stainless steel mix tank. The suspension was agitated until all solids dissolved. The resulting solution was passed through a charcoal cartridge and collected into a glass bottle to provide a clear, colorless solution. (Stream 1)
2. Sodium nitrite (1.097 kg) and water (4.005 kg) were added to a glass bottle and stirred until the solids dissolved. (Stream 2)
3. Toluenesulfonyl chloride (3.088 kg) was added to a carboy and blanketed with nitrogen gas. 1,4-Dioxane (18.22 kg) and 2-methyltetrahydrofuran (6.290 kg) were added and the suspension was stirred to dissolve the solids. (Stream 3)
4. Potassium acetate (5.067 kg), water (25.75 kg), hydroxylammonium chloride (1.073 kg), and 1,4-dioxane (12.93 kg) were added to a glass carboy. The suspension was stirred until all solids dissolved. (Stream 4)
5. Each feed stream was connected to a pump appropriate for pumping it.
6. The pumps for streams 1 (18.8 mL/min), 2 (9.59 mL/min), 3 (57 mL/min) 4 (47 mL/min), and toluene (20 mL/min), as well as the motors for the first and second centrifuges were started. The average residence times are 1.75 min, 1.75 min, 0.38 min, and 1.89 min for steps a, b, c, and d, respectively. Heat exchange functions were powered on.
7. The reaction mixture was discarded until equilibration of flows and completion of all chemical conversions was observed, as determined by HPLC, at which point the receiving vessel was changed and the reaction mixture was collected. The typical conversion under these exact conditions is >97 HPLC A % at 210 nm (A % 4 vs A % 2+A % 3).
8. The aqueous and organic layers were collected until any of the starting material solutions was exhausted or until the desired run time was achieved. Each collection container was assayed by HPLC to ensure the process operated normally (typical aqueous concentration=0.1-0.2 wt % oxadiazole 4, typical organic concentration=2.2-2.4 wt %).
9. Zinc diacetate dihydrate (3.230 kg) was charged to an inerted batch reactor. The organic layers were charged and the suspension was agitated.

10. Ethyl acetoacetate (4.788 kg) was added to the batch reactor.
11. The batch was heated to 70° C. for 24 h.
12. Once the target conversion was met, the suspension was distilled and 1,4-dioxane was added until the 2-MeTHF and toluene had been removed.
13. Water was added to maintain the internal batch temperature between 65 and 70° C.
14. The batch was aged at 65-70° C. for 20 minutes after crystallization occurred.
15. The batch was cooled to room temperature over ~1 h.
16. The batch was filtered.
17. The cake was washed with water (4.000 kg).
18. The cake was transferred to a tray and dried at 40° C. for 16 h under a purge of nitrogen gas to afford a solid (35% overall yield, 1.170 kg)

$^1$H NMR (400 MHz, DMSO-d6) δ (ppm)=8.61 (bs, 2H), 4.35 (q, 2H), 2.62 (s, 3H), 1.34 (t, 3H).

HPLC Area %>98% at 210 nm.

The invention claimed is:

1. Process for manufacturing alkyl 7-amino-5-methyl-[1,2,5]-oxadiazolo-[3,4-b]pyridine-carboxylate 5

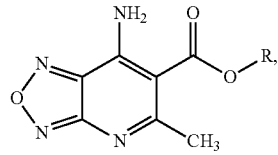

wherein R is $C_{1-3}$-alkyl,
by combining an integrated continuous flow system under overpressure, with a batch reactor, said process comprising the following steps:
(a) reacting malononitrile with sodium nitrite in the presence of a suitable acid in a suitable solvent;
(b) reacting the reaction mixture obtained by step (a) with a suitable toluenesulfonic acid derivative to obtain compound 2;

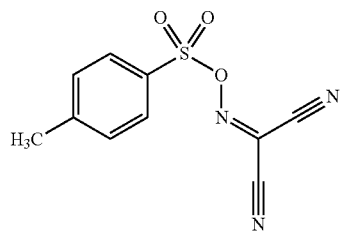

(c) reacting compound 2 in a suitable solvent with hydroxylamine or a suitable hydroxylamine salt to obtain compound 3;

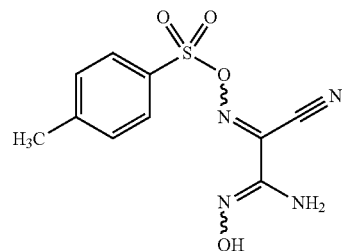

(d) cyclisation of compound 3 in the presence of a base under heating to about 120° C. in a suitable solvent to obtain the oxadiazole 4;

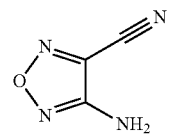

(e) removal of the by-product water formed in step (d) from the reaction mixture by phase separation;
(f) in situ-condensation of compound 4 in the reaction mixture obtained after step (e) with the appropriate beta-keto ester of formula

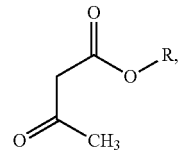

wherein R is $C_{1-3}$-alkyl, in a batch reactor in the presence of a Lewis acid in a suitable solvent; and
(g) isolating compound 5 from the batch reactor.

2. The process according to claim 1 characterized in that in step (a), hydrochloric acid, hydrobromic acid or acetic acid are used as the suitable acid, and water is used as a solvent.

3. The process according to claim 1 characterized in that step (a) is carried out under an overpressure of at least 2 bar at a temperature of 20 to 40° C. for 15 sec to 5 min.

4. The process according to claim 1 characterized in that in step (a), acetic acid is used as the suitable acid, and water is used as a solvent at a temperature about 30° C. for 15 sec to 5 min.

5. The process according to claim 1 characterized in that in step (b) the suitable toluenesulfonic acid derivative is toluenesulfonic acid anhydride or toluenesulfonic acid chloride, and the reaction is carried out at a temperature of 20 to 40° C. for 15 sec to 5 min.

6. The process according to claim 1 characterized in that in step (b) the suitable toluenesulfonic acid derivative is toluenesulfonic acid chloride, and the reaction is carried out at a temperature of about 30° C. for 15 sec to 5 min.

7. The process according to claim 1 characterized in that in step (c), the reaction is carried out at a temperature of 20 to 40° C. for 15 s to 5 min, using a solvent comprising ethers, water, or mixtures thereof.

8. The process according to claim 1 characterized in that in step (c), the reaction is carried out at a temperature of about 30° C. for 15 s to 5 min; using a solvent comprising 2-methyl-tetrahydrofuran, 1,4-dioxane, water, or mixtures thereof; and the suitable hydroxylamine salt is hydroxylammonium chloride.

9. The process according to claim 1 characterized in that in step (d), the cyclisation is carried out in the presence of triethylamine, an alkali acetate, an alkali carbonate or an alkali hydrogencarbonate; using a solvent comprising ethers, water, or mixtures thereof; at a temperature of 110 to 130° C. for 15 s to 5 min; and under a pressure of at least 2 bar.

10. The process according to claim 1 characterized in that in step (d), the alkali acetate is selected from the group consisting of lithium acetate, sodium acetate, and potassium acetate; the alkali carbonate is selected from the group consisting of sodium carbonate and potassium carbonate; and the alkali hydrogencarbonate is selected from the group consisting of sodium hydrogencarbonate and potassium hydrogencarbonate; and using 1,4-dioxane or 2-methyl-tetrahydrofuran as a solvent.

11. The process according to claim 1 characterized in that in step (e), water is removed by extraction at about 20 to 45° C., using a non-polar extraction solvent selected from the group consisting of toluene, methyl tert-butyl ether, heptane, and isopropyl acetate.

12. The process according to claim 1 characterized in that in step (e), water is continuously removed by extraction at about 20 to 45° C. using toluene or methyl tert-butyl ether as an extraction solvent.

13. The process according to claim 1 characterized in that in step (e), water is continuously removed by extraction at about 30° C. using methyl tert-butyl ether as extraction solvent.

14. The process according to claim 1 characterized in that in step (e), water is removed in a batch-process at about 20° C. using methyl tert-butyl ether as an extraction solvent.

15. The process according to claim 1 characterized in that in step (1), the in situ-condensation is carried out in the presence of a zinc salt as the Lewis acid at a temperature of 60 to 100° C. for 2 to 24 hours, in a solvent selected from the group consisting of an ether, alcohol, non-polar solvents, and mixtures thereof.

16. The process according to claim 1 characterized in that in step (1), the in situ-condensation is carried out in the presence of zinc acetate as the Lewis acid at a temperature of 60 to 100° C. for 2 to 24 hours, in a solvent selected from the group consisting of 1,4-dioxane, 2-methyl-tetrahydrofuran, methyl tert-butyl ether, ethanol, and mixtures thereof.

17. The process according to claim 1 characterized in that in step (g), compound 5 is precipitated via addition of an antisolvent and then isolated via filtration.

18. The process according to claim 1 characterized in that in step (g), compound 5 is precipitated via addition of water and then isolated via filtration.

19. The process according to claim 1 wherein R is ethyl.

* * * * *